United States Patent [19]
Belmont

[11] Patent Number: 6,037,476
[45] Date of Patent: Mar. 14, 2000

[54] PROCESS FOR MAKING CYCLIC IMIDES

[75] Inventor: Stephen E. Belmont, Baton Rouge, La.

[73] Assignee: Albemarle Corporation, Richmond, Va.

[21] Appl. No.: 09/287,696

[22] Filed: Apr. 6, 1999

[51] Int. Cl.[7] .................................................. C07D 209/48
[52] U.S. Cl. ............................................................. 548/480
[58] Field of Search ............................................. 548/480

[56] References Cited

U.S. PATENT DOCUMENTS

| | | | |
|---|---|---|---|
| 2,846,382 | 8/1958 | Allen | 204/75 |
| 3,931,243 | 1/1976 | Paustian et al. | 260/346.7 |
| 5,047,553 | 9/1991 | Nowak et al. | 548/476 |
| 5,196,590 | 3/1993 | Oi et al. | 562/493 |
| 5,596,104 | 1/1997 | O'Reilly et al. | 548/480 |

OTHER PUBLICATIONS

Rice et al., "N–Alkyl Imides and Their Reduction by Means of Lithium Aluminum Hydride", J. Org. Chem, vol. 19, 1954, pp. 884–893.

Rosen et al., "Tetrachloroisoindolines and Related Systems. Alkylation Reactions and Inductive Effects", J. Am. Chem. Soc., vol. 79, 1957, pp. 3167–3174.

Kreher et al., "Symmetrisch substituierte 2–Alkyl–2H–isoindole", Chem. Ber., vol. 123, 1990, pp. 1719–1727.

Grogan et al., "Bicyclic Imides and Isoindolines", J. Med. Chem., vol. 6, 1963, pp. 802–805.

Hargreaves et al., "Cyclic Carboxylic Monoimides", Chemical Reviews, vol. 70, No. 4, 1970, pp. 439–469.

Robinson et al., "Dichloromethylenation of Substituted 1 H–Isoindole–1,3–(2H)–diones (Phthalimides)", Journal of Heterocyclic Chemistry, 1995, vol. 32, pp. 783–785.

Eaton et al., "Hydrolysis in the Absense of Bulk Water 1. Chemoselective Hydrolysis of Amides Using Tetrahalophthalic Anhydrides", Tetrahedron Letters, 1988, vol. 29, No. 50, pp. 6553–6556.

*Primary Examiner*—Joseph McKane
*Attorney, Agent, or Firm*—Philip M. Pippenger

[57] ABSTRACT

A process of producing cyclic imides from cyclic anhydrides is described. Despite the fact that an acid anhydride is reacted with a primary amine in the presence of both water and an acid, the reaction is materially unaffected by acid-catalyzed hydrolysis of the anhydride. Thus a reaction is provided which eliminates the handling and processing problems associated with performing reactions under anhydrous conditions, and which can provide a product of high purity in very high yield.

35 Claims, No Drawings

PROCESS FOR MAKING CYCLIC IMIDES

BACKGROUND

Cyclic imides are useful as intermediates in the production of important organic molecules. For example, the Floxacin antibiotics, a widely used, commercially important family of synthetic compounds, can be synthesized from relatively inexpensive phthalic anhydrides by using phthalimides prepared according to the process of this invention.

Though the production of cyclic imides by the reaction of cyclic anhydrides with primary amines has been known for decades, the process has deficiencies in important areas. Despite the fact that the production of cyclic imides is an endeavor of commercial importance, the deficiencies have persisted.

For instance, a method from the literature for producing N-methyl tetrachlorophthalimide from tetrachlorophthalic anhydride is by the direct reaction of tetrachlorophthalic anhydride with methylarnine in an aprotic solvent at temperatures as high as 200° C. Conditions are typically anhydrous due to the potential for the anhydride to hydrolyze and give rise to a dicarboxylic acid. The formation of the anhydride is a reaction which competes with the formation of the cyclic imide, thus diminishing yield and purity of the desired product.

The use of anhydrous conditions puts a severe limitation on the large scale production of many cyclic imides, as well as the use of many cyclic imides in stepwise industrial processes, for it necessitates the handling of solid and gaseous reactants. In general, the handling of solids and gases is significantly more costly and labor intensive than the handling of aqueous solutions. Thus, the utility of the cyclic imide formation reaction is encumbered by a constraint which limits its usefulness in organic synthesis, especially when carried out on an industrial scale. Furthermore, the use of anhydrous conditions is typically only a partial solution, for even under anhydrous conditions, other ring-opened impurities are often formed in significant amounts.

It has previously been demonstrated that the use of carboxylic acids as solvents in the cyclic imide formation reaction favors the formation of the cyclic imide as opposed to the formation of ring-opened impurities, thus improving both purity and yield. However, even when using carboxylic acid solvents, literature methods adhere to anhydrous conditions. In light of the fact that acidic conditions are known to exacerbate the tendency of anhydrides to undergo hydrolysis in the presence of water, it is not surprising that methods which utilize carboxylic acids to produce cyclic imides in high product purity and yield also maintain anhydrous conditions.

It would represent a significant advance in the state of the art if a method of preparing cyclic imides could be found which eliminates the handling problems associated with solids and gases while maintaining the excellent yield and purity produced in the presence of a carboxylic acid solvent.

SUMMARY OF THE INVENTION

It has been found, surprisingly, that when the cyclic imide-forming reaction of cyclic anhydrides and primary amines is carried out using aqueous reactants in the presence of a carboxylic acid solvent, handling of solid and gaseous reactants is avoided, and high purity and yield can be achieved. Despite the tendency for acids to catalyze the hydrolysis reaction of acid anhydrides and water, the process of this invention proceeds readily, without any material interference from this competitive hydrolysis side reaction.

Accordingly, one embodiment of this invention is a process for producing cyclic imides, which comprises A) contacting (1) a cyclic carboxylic acid anhydride with (2) a water-soluble primary amine, in the presence of (3) a water-soluble carboxylic acid, and (4) water; and B) allowing and/or causing the mixture to undergo reaction at one or more temperatures such that a cyclic imide is formed. The reaction in B) can proceed adiabatically if a sufficient exotherm is produced. However, in most cases, addition of thermal energy (heating) is desirable.

In a preferred embodiment, an aqueous solution of a primary amine is added to a mixture comprised of the acid anhydride and the carboxylic acid.

Another preferred embodiment of this invention is a process for preparing cyclic imides, which process comprises: A) combining (1) a cyclic carboxylic acid anhydride and (2) a water-soluble carboxylic acid; B) adding an aqueous solution of (3) a water-soluble primary amine; and C) heating the mixture at one or more temperatures such that a cyclic imide is formed.

In yet other particularly preferred embodiments, the above cyclic carboxylic anhydride, carboxylic acid and primary amine are tetrachlorophthalic anhydride, acetic acid and methylamine, respectively.

The above and other embodiments will be apparent from the ensuing description and appended claims.

FURTHER DESCRIPTION

Cyclic anhydrides which can be used in the process of this invention comprise the anhydrides of aliphatic, alicyclic, aromatic or heterocyclic dibasic carboxylic acids. Suitable acid anhydrides include, but are not limited to, 1,2,4,5-benzenetetracarboxylic acid anhydride, 1,2,4-benzene-tricarboxylic anhydride, 3,3',4,4'-benzophenonetetracarboxylic dianhydride, 3,4-coronenedicarboxylic anhydride, homophthalic anhydride, mellitic trianhydride, 1,4,5,8-naphthalenetetracarboxylic dianhydride, 1,8-naphthalic anhydride, 3-nitro-1,8-naphthalic anhydride, phthalic anhydride, tetrabromophthalic anhydride, tetrachlorophthalic anhydride, tetraphenyl phthalic anhydride, 3-nitrophthalic anhydride, bromomaleic anhydride, chloromaleic anhydride, citraconic anhydride, glutaric anhydride, 2,2-dimethylglutaric anhydride, 3-methyl-glutaric anhydride, 3,3-tetra-methyleneglutaric anhydride, 2-phenyl glutaric anhydride, 2,3-dimethylmaleic anhydride, 2-dodecen-1-ylsuccinic anhydride, succinic anhydride, methylsuccinic anhydride, endo-bicyclo[2,2,2] octa-5-ene-2,3-dicarboxylic anhydride, bicyclo[2,2,2]oct-7-ene-2,3,5,6-tetracarboxylic-2,3,5,6-dianhydride, camphoric anhydride, cis-1,2-cyclobutanedicarboxylic anhydride, cis-1,2-cyclohexanedicarboxylic anhydride, cis,cis,cis,cis-1,2,3,4-cyclopen-tanetetracarboxylic dianhydride, 1,4,5,6,7,7-hexachloro-5-norbornene-2,3-dicarboxylic anhydride, 4-methyl-1,2-cyclohexanedicarboxylic anhydride, cis-1,2,3,6-tetrahydrophthalic anhydride, isatoic anhydride, 5-chloroisatoic anhydride, diglycolic anhydride, 2,3-pyridine-dicarboxylic anhydride and the like.

More preferred are phthalic acid anhydrides which can, if desired, bear one or more substituents on the aromatic ring to which the anhydride functionality is attached, i.e. one or more of the following positions: 3, 4, 5, and 6. Nonlimiting examples include phthalic anhydride, tetrabromophthalic anhydride, tetrachlorophthalic anhydride, tetraphenyl phthalic anhydride, 3-nitrophthalic anhydride. Even more preferred are the halophthalic anhydrides. Nonlimiting examples of such are tetrabromophthalic anhydride, tetrachlorophthalic anhydride. Most preferred is 3,4,5,6-tetrachlorophthalic anhydride.

It is preferable that the water and the acid anhydride be present in the reaction mixture in a mole ratio in the range of about 0.5 moles of water per mole of acid anhydride to about 10 moles of water per mole of acid anhydride. More preferable is a mole ratio in the range of about 2 moles of water per mole of acid anhydride to about 4 moles of water per mole of acid anhydride. Most preferable is a mole ratio of about 3.

The primary amines which can be used in the process of this invention are water-soluble primary monoamines or water-soluble polyamines with at least one primary amine functionality. Preferable are aliphatic, cycloaliphatic and aromatic amines, especially the monoamines. Halogen atoms, hydroxyl, alkoxy and/or other functional substituents which do not interfere with the desired reaction are permitted. Likewise, replacement of hydrocarbyl carbon atoms with heteroatoms is permitted if cyclic imide formation reactivity is retained. Nonlimiting examples of primary amines and primary diamines which can be used are methylamine, ethylamine, 2-chloroethylamine, n-propylamine, isopropylamine, allylamine n-butylamine, tert-butylamine, d and l isomers of sec-butylamine, isopentylamine, cyclohexylamine, benzylamine, 3-aminopyridine, 4-aminopyridine, ethylene diamine, N,N-dimethylethylenediamine and similar examples. Aniline and many ring-substituted anilines are also suitable. Nonlimiting examples include 3,4-dihydroxyaniline, 2,3-dimethoxyaniline, p-methoxyaniline, 4-methylaminoaniline, and similar compounds. Preferred are aliphatic primary amines of up to about 10 carbon atoms. More preferred are aliphatic primary amines of up to about 8 carbon atoms. Examples of such are benzylamine, phenylamine, butylamine, propylamine, ethylamine and methylamine. Most preferred is methylamine.

The primary amine and the acid anhydride react in a one to one ratio, thus the reactant which is used in lesser equivalent quantities is the limiting reagent. It is preferable that the primary amine functionality and the anhydride functionality are present in an equivalent ratio in the range of from about 1 equivalent of amine per equivalent of anhydride to about 2 equivalents of amine per equivalent of anhydride. More preferable is an equivalent ratio in the range of from about 1.1 equivalents of amine per equivalent of anhydride to about 1.3 equivalents of amine per equivalent of anhydride. Most preferable is a mole ratio of about 1.15 equivalents of amine per equivalent of anhydride.

The carboxylic acids used in the process of this invention are water-soluble aliphatic carboxylic acids which are liquids at reaction temperatures. Halogen atoms and other substituents that do not interfere with the described reaction are permitted provided that they do not render the acid insoluble in water at reaction temperatures. Nonlimiting examples of such are formic acid, acetic acid, trichloroacetic acid, trifluoroacetic acid, propionic acid, butyric acid, isobutyric acid, valeric acid, and similar compounds. Preferably, the carboxylic acid used is an aliphatic acid which contains up to about 10 carbon atoms. Suitable examples include formic acid, trichloroacetic acid, trifluoroacetic acid and propionic acid. More preferred are carboxylic acids which contain up to about 4 carbon atoms, such as propionic acid and acetic acid. Most preferred is acetic acid.

Typically, the molar ratio of water to carboxylic acid is in the range of about 0.1 mole of water per mole of carboxylic acid to about 1 mole of water per mole of carboxylic acid. More preferable is a mole ratio of water to carboxylic acid in the range of about 0.15 mole of water per mole of carboxylic acid to about 0.5 mole of water per mole of carboxylic acid. Most preferable is a mole ratio of about 0.25 mole of water per mole of carboxylic acid.

Typically, the primary amine and the carboxylic acid should have at least moderate water-solubilities in order for the benefits of the process of this invention to be fully realized. Water-solubility at reaction temperatures is especially important. Although even compounds with very low water-solubility can react in the process, it is desirable that they be soluble to the extent of at least about 3 grams per 100 mL of distilled water at 20° C.

In general, any mode and sequence of mixing the reaction components can be used provided that in the absence of the primary amine, the water and the cyclic anhydride are not brought together under conditions whereby most, if not all, of the anhydride would be converted to the corresponding dicarboxylic acid.

However, it has been observed that in some cases a concrete-like solid can form upon combining the acid anhydride and the primary amine. Such solids can be difficult to handle. In order to avoid the formation of these bulky solids, it is preferable to avoid combining the acid anhydride with the amine in the absence of water, acid, or both water and acid.

Nevertheless, there are a number of ways in which the reaction components can be brought together in conducting the process. For example, the primary amine, the carboxylic acid or both can be introduced to the reaction mixture in aqueous form. If only the primary amine is introduced as an aqueous solution, the amine solution and the carboxylic acid can be combined with the acid anhydride in either order or concurrently. If only the carboxylic acid or both the carboxylic acid and the primary amine are introduced as aqueous solutions, it is preferred to add the amine and the carboxylic acid concurrently in order to avoid acid-catalyzed hydrolysis of the acid anhydride. However, it is also possible to add the amine before adding the carboxylic acid solution. Preferably the reactants are combined incrementally over a period of time in order to prevent uncontrolled localized heat formation. For example, an aqueous solution of the amine can be added to the anhydride/carboxylic acid mixture.

Although the initial step in the cyclic imide formation reaction tends to be exothermic, typically the heat formed in the initial step in the reaction is not sufficient to enable completion of the cyclic imide forming reaction, and the application of heat is therefore beneficial and highly preferred.

Heat can be supplied to the reaction in many ways. A mixture of the reaction components can be formed and subsequently heated. Alternatively, some of the reaction components can be mixed and heated, with the remaining components added to the preheated mixture at a later time. For example, an aqueous solution of the primary amine can be added to a preheated acid anhydride/carboxylic acid mixture. Other examples are the addition of an acid anhydride/carboxylic acid mixture to a preheated aqueous primary amine solution, or the addition of the acid anhydride to a preheated aqueous primary amine/carboxylic acid mixture. However, it is preferable to avoid heating an acid anhydride/water mixture, with or without the carboxylic acid, in the absence of the primary amine.

As the initial step in the cyclic imide formation reaction tends to be exothermic, it can be preferable to combine the reactants together over a period of time in order to control the rate of heat formation. For example, an aqueous solution of the amine can be added dropwise to an acid anhydride/carboxylic acid mixture.

It is desirable to heat the reaction components to a temperature in the range of from about 60° C. to about 250° C. More desirable is a temperature in the range of about 80° C. to about 150° C. Most desirable is a temperature of about 110° C.

Upon completion of the reaction the cyclic imide may be separated from the reaction mixture by mechanical filtration, centrifugation, decantation or another suitable means of separation. A degree of purification of the imide may be accomplished by recrystallization in a suitable solvent, or by rinsing of the solid with acetic acid or other similar solvents.

The following example demonstrates the high purity and yield attainable in aqueous media.

EXAMPLE

Preparation of N-methyltetrachlorophthalimide in Aqueous Media

Tetrachlorophthalic anhydride (1250 g, 4.37 mol) was suspended in glacial acetic acid (3.0 L) in a 5 L 3-neck flask with condenser and mechanical stirrer attached. Methylamine (40% solution in water, 433 mL, 5.0 mol) was added over 3 minutes, resulting in an exotherm to 55° C. A heating mantle was used to heat the reaction to mild reflux (110–113° C.) for 5 hr. After cooling to ambient, the product was collected on a sintered funnel, washed with acetic acid (500 mL), and dried at 40–50° C. under high vacuum to constant weight, affording 1292 g (99%) of white crystalline material (99.6% by GC), MP (uncorrected)=153–155° C.

It is to be understood that the reactants and components referred to by chemical name or by formula anywhere in the specification or claims hereof, whether referred to in the singular or plural, are identified as they exist prior to coming into contact with another substance referred to by chemical name or chemical type (e.g., another reactant, a solvent, or etc.). It matters not what preliminary chemical changes, transformations and/or reactions, if any, take place in the resulting mixture or solution or reaction medium as such changes, transformations and/or reactions are the natural result of bringing the specified reactants and/or components together under the conditions called for pursuant to this disclosure. Thus the reactants and components are identified as ingredients to be brought together in connection with performing a desired chemical reaction or in forming a mixture to be used in conducting a desired reaction. Accordingly, even though the claims hereinafter may refer to substances, components and/or ingredients in the present tense ("comprises", "is", etc.), the reference is to the substance, component or ingredient just as it existed at the time just before it was first contacted, blended or mixed with one or more other substances, components and/or ingredients in accordance with the present disclosure. Thus the fact that a substance, component or ingredient may have lost its original identity through a chemical reaction or transformation through the course of contacting, blending or mixing operations, if conducted in accordance with this disclosure and with the application of common sense and the ordinary skill of a chemist, is wholly immaterial for an accurate understanding and appreciation of the true meaning and substance of this disclosure and the claims thereof.

This invention is susceptible to considerable variation in its practice. Therefore the foregoing description is not intended to limit, and should not be construed as limiting, the invention to the particular exemplifications presented hereinabove. Rather, what is intended to be covered is as set forth in the ensuing claims and the equivalents thereof permitted as a matter of law.

That which is claimed is:

1. A process of producing cyclic imides, which process comprises:

A) contacting (1) a cyclic carboxylic acid anhydride with (2) a water soluble primary amine in the presence of (3) a water soluble carboxylic acid, and (4) water; and B) allowing and/or causing the mixture to undergo reaction at one or more temperatures such that a cyclic imide is formed.

2. A process as in claim 1 wherein the mole ratio of (4) to (1) is in the range of about 0.5 mole of (4) per mole of (1) to about 10 moles of (4) per mole of (1).

3. A process as in claim 1 wherein the mole ratio of (2) to (1) is in the range of about 1 mole of (2) per mole of (1) to about 2 moles of (2) per mole of (1).

4. A process as in claim 1 wherein the mole ratio of (4) to (3) is in the range of about 0.1 mole of (4) per mole of (3) to about 1 mole of (4) per mole of (3).

5. A process as in claim 1 wherein the temperature is in the range of about 60° C. to about 250° C.

6. A process as in claim 1 wherein (1) is the anhydride of an aliphatic, alicyclic, aromatic or heterocyclic dibasic carboxylic acid.

7. A process as in claim 1 wherein (2) is a water soluble primary amine or a water soluble polyamine with at least one primary amine functionality which contains less than about 10 carbon atoms.

8. A process as in claim 1 wherein (3) is a water soluble, hydrocarbyl carboxylic acid which contains less than about 10 carbon atoms.

9. A process as in claim 1 wherein the mole ratio of (4) to (1) is in the range of about 2 moles of (4) per mole of (1) to about 4 moles of (4) per mole of (1).

10. A process as in claim 1 wherein the mole ratio of (2) to (1) is in the range of about 1.1 moles of (2) per mole of (1) to about 1.3 moles of (2) per mole of (1).

11. A process as in claim 1 wherein the mole ratio of (4) to (3) is in the range of about 0.15 mole of (4) per mole of (3) to about 0.5 moles of (4) per mole of (3).

12. A process as in claim 1 wherein the temperature is in the range of about 80° C. to about 150° C.

13. A process as in claim 1 wherein (1) is a phthalic anhydride in which the aromatic ring is, optionally, substituted at one or more of the following positions: 3, 4, 5, and 6.

14. A process as in claim 1 wherein (1) is a halophthalic anhydride.

15. A process as in claim 1 wherein (2) is a water soluble, aliphatic primary amine or a water soluble, aliphatic polyamine with at least one primary amine functionality, which contains less than about 8 carbon atoms.

16. A process as in claim 1 wherein (3) is a water soluble, hydrocarbyl carboxylic acid which contains less than about 4 carbon atoms.

17. A process as in claim 1 wherein the mole ratio of (4) to (1) is about 3 moles of (4) per mole of (1), the ratio of (2) to (1) is about 1.15 moles of (2) per mole of (1), the ratio of (4) to (3) is about 0.25 moles of (4) per mole of (3); wherein (1) is a phthalic anhydride in which the aromatic ring is, optionally, substituted at one or more of the positions not connected to the anhydride functionality; wherein (2) is a water soluble, hydrocarbyl primary amine or a water soluble, hydrocarbyl polyamine with at wherein (3) is a water soluble, hydrocarbyl carboxylic acid which contains up to about 4 carbon atoms.

18. A process as in claim 17 wherein (1) is 3,4,5,6-tetrachlorophthalic anhydride.

19. A process as in claim 17 wherein (2) is methylamine.

20. A process as in claim 17 wherein (3) is acetic acid.

21. A process as in claim 17 wherein (1) is 3,4,5,6-tetrachlorophthalic anhydride, (2) is methylamine, and (3) is acetic acid, wherein the mole ratio of water to 3,4,5,6-tetrachlorophthalic anhydride is about 3 moles of water per mole of 3,4,5,6-tetrachlorophthalic anhydride, wherein the mole ratio of methylamine to 3,4,5,6-tetrachlorophthalic anhydride is about 1.15 moles of methylamine per mole of 3,4,5,6-tetrachlorophthalic anhydride, wherein the mole ratio of water to acetic acid is about 0.25 moles of water per mole of acetic acid, and wherein the temperature is about 110° C.

22. A process which comprises heating an aqueous mixture comprised of 3,4,5,6-tetrachlorophthalic anhydride, methylamine and acetic acid to a temperature of about 110° C. such that N-methyl-3,4,5,6-tetrachlorophthalic anhydride is formed.

23. A process as in claim 22 wherein the mole ratio of water to 3,4,5,6-tetrachlorophthalic anhydride is about 3 moles of water per mole of 3,4,5,6-tetrachlorophthalic anhydride, wherein the mole ratio of methylamine to 3,4,5,6-tetrachlorophthalic anhydride is about 1.15 moles of methylamine per mole of 3,4,5,6-tetrachlorophthalic anhydride, wherein the mole ratio of water to acetic acid is about 0.25 mole of water per mole of acetic acid, and wherein the temperature is about 110° C.

24. A process of preparing cyclic imides, which process comprises:

A) suspending (1) a cyclic carboxylic acid anhydride in (2) a water soluble carboxylic acid;

B) adding an aqueous solution of (3) a water soluble primary amine; and

C) heating the mixture at one or more temperatures such that cyclic imides are formed.

25. A process as in claim 24 wherein (1) is 3,4,5,6-tetrachlorophthalic anhydride, (2) is methylamine, (3) is acetic acid, wherein the mixture of C) has a mole ratio of water to (1) of about 3 moles of water per mole of (1), a mole ratio of (3) to (1) of about 1.15 moles of (3) per mole of (1), the mole ratio of water to (2) is about 0.25 moles of water per mole of (2); wherein (3) is added at the rate of about 0.01 equivalent per equivalent of acid anhydride per second; and wherein the temperature in C is about 110° C.

26. A process of preparing a cyclic imide, said process comprising reacting a cyclic carboxylic acid anhydride and a water-soluble primary amine in a liquid medium comprising a water-soluble carboxylic acid and water such that a cyclic imide is formed.

27. A process as in claim 26 wherein the primary amine is methylamine.

28. A process as in claim 27 wherein the carboxylic acid is acetic acid.

29. A process as in claim 28 wherein the cyclic carboxylic acid anhydride is 3,4,5,6-tetrachlorophthalic acid anhydride.

30. A process as in claim 29 wherein the cyclic acid anhydride and the water are present during the reaction in a mole ratio in the range of about 2 moles of water per mole of cyclic acid anhydride to about 4 moles of water per mole of cyclic acid anhydride.

31. A process as in claim 30 wherein the primary amine and the acid anhydride are present during the reaction in a mole ratio in the range of about 1.1 moles of amine per mole of cyclic acid anhydride to about 1.3 moles of amine per mole of cyclic acid anhydride.

32. A process as in claim 31 wherein the carboxylic acid and the water are present during the reaction in a mole ratio in the range of about 0.15 mole of water per mole of carboxylic acid to about 0.5 mole of water per mole of carboxylic acid.

33. A process as in claim 29 wherein the cyclic acid anhydride and the water are present during the reaction in a mole ratio of about 3 moles of water per mole of cyclic acid anhydride.

34. A process as in claim 33 wherein the primary amine and the acid anhydride are present during the reaction in a mole ratio of about 1.15 mole of amine per mole of cyclic acid anhydride.

35. A process as in claim 34 wherein the carboxylic acid and the water are present during the reaction in a mole ratio of about 0.25 mole of water per mole of carboxylic acid.

* * * * *